United States Patent [19]

Hjerten

[11] Patent Number: 5,961,834
[45] Date of Patent: *Oct. 5, 1999

[54] SIMPLE MICRO METHOD FOR CONCENTRATION AND DESALTING UTILIZING A HOLLOW FIBER, WITH SPECIAL REFERENCE TO CAPILLARY ELECTROPHORESIS

[75] Inventor: Vilhelm Einar Stellan Hjerten, Uppsala, Sweden

[73] Assignee: Bio-Rad Laboratories, Inc., Hercules, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/859,008

[22] Filed: May 20, 1997

Related U.S. Application Data

[63] Continuation-in-part of application No. 08/772,325, Dec. 23, 1996, abandoned.

[51] Int. Cl.[6] .............................. B01D 61/00; B01D 63/02
[52] U.S. Cl. ............... 210/649; 210/321.78; 210/321.87; 210/650; 436/174; 436/177; 436/178
[58] Field of Search ..................... 210/649, 650, 210/651, 652, 621.78, 621.87, 500.23; 436/174, 177, 178

[56] References Cited

U.S. PATENT DOCUMENTS

| | | | |
|---|---|---|---|
| 4,416,772 | 11/1983 | Sato et al. | 210/137 |
| 4,448,691 | 5/1984 | Davis | 210/656 |
| 4,568,488 | 2/1986 | Lee-Huang | 424/99 |
| 4,609,464 | 9/1986 | Aoyagi et al. | 210/500.23 |
| 4,690,754 | 9/1987 | Koyama et al. | 210/500.23 |
| 4,708,799 | 11/1987 | Gerlach et al. | 210/500.23 |
| 4,794,088 | 12/1988 | Miyaki et al. | 210/500.23 |
| 4,957,620 | 9/1990 | Cussler | 210/500.23 |
| 5,160,625 | 11/1992 | Jonsson et al. | 210/500.23 |
| 5,202,023 | 4/1993 | Trimmer et al. | 210/500.23 |
| 5,211,850 | 5/1993 | Shettigar et al. | 210/500.23 |
| 5,259,971 | 11/1993 | Morse et al. | 210/650 |
| 5,279,972 | 1/1994 | Heckenberg et al. | 210/500.23 |
| 5,340,480 | 8/1994 | Kawata et al. | 210/500.23 |
| 5,505,831 | 4/1996 | Liao et al. | 204/451 |
| 5,578,204 | 11/1996 | Barholmes et al. | 210/500.23 |

Primary Examiner—John Kim
Attorney, Agent, or Firm—Townsend and Townsend and Crew LLP

[57] ABSTRACT

A dilute aqueous solution in microvolume quantity containing water soluble substances is concentrated by placing the solution in a length of hollow fiber whose wall contains pores sized to selectively pass water, while replenishing the fiber volume with additional solution at a rate approximately equal to the rate that the water passes through the fiber wall. A zone of concentrated solution is formed within the fiber, and the concentrated solution is then recoverable from the zone.

28 Claims, 10 Drawing Sheets

SIMPLE MICRO METHOD FOR CONCENTRATION AND DESALTING UTILIZING A HOLLOW FIBER, WITH SPECIAL REFERENCE TO CAPILLARY ELECTROPHORESIS

This application is a continuation-in-part of U.S. patent application Ser. No. 08/772,325, filed Dec. 23, 1996, abandoned, the disclosure of which is incorporated by reference.

BACKGROUND OF INVENTION

An ideal analytical micro method permit studies not only of samples of minute volume but also of low concentration. The former requirement is fulfilled by electrophoresis and chromatography in the capillary format, but not always the latter. The reason need not be that the original concentration of the analytes in the sample is extremely low but that the concentration of the analytes decreases drastically due to adsorption onto all surfaces with which they come into contact. However, this adsorption seldom alters the concentration of all analytes to the same degree, and therefore often changes the quantitative composition of the sample. The problem is particularly great with small sample volumes when the concentration of the solutes is so low that an enrichment is required for detection.

Concentration of solutes in small volumes offers special problems. The difficulties are particularly great when the sample concentration is extremely low because the adsorption onto the surfaces with which the solutes come into contact may be very strong. The adsorption not only decreases the original sample concentration but also often alters the relative concentrations of the solute, causing serious deviations from the original composition of the sample.

Bundles of a great number of hollow fibers are used routinely for cross-flow ultra-dialysis both on the laboratory and industrial scale. Such bundles have been employed also for continuous, on-line dialysis of chromatographic eluates against water for desalting against an appropriate solution for buffer exchange and against polyethylene glycol for enrichment of macromolecules from chromatographic columns. Kaufmann, M.; Schwarz, T.; Bartholmes, P. J. Chromatogr. 1993, 639, 33. Hollow fibers can also serve as separation chambers in field-flow-fractionation. Lee, H. L.; Lightfoot, E. N. Sep. Sci. 1976, 11, 417. Jonsson, J. A.; Carlshaf, A. Anal, Chem. 1989, 61, 11. A novel concentration method and apparatus of this invention uses a hollow fiber filled with the dilute sample solution. The technique is based on the transport of water out of the fiber through the pores in its wall and has the advantage that solute adsorption is negligible. Thus, the present invention provides a simple micro method for the concentration of analytes without disturbing adsorption. The method is based on the transport of water by evaporation or the Donnan effect through the pores in the wall of a single hollow fiber filled with the sample. The fiber can be used not only for the concentration of macromolecules but also for low-molecular-weight compounds and inorganic ions. The fiber also permits equilibration of polymer against any solution.

SUMMARY OF INVENTION

A novel apparatus for the concentration of microvolumes of a dilute aqueous solution of water soluble biological molecules comprising a discrete strand of hollow fiber adapted to receive an initial amount of said solution, the walls of the fiber containing pores sized to pass water therethrough, and means associated with said strand for subsequently replenishing the volume of liquid within the strand in a manner approximating the rate of water passing through said wall.

The method of concentration microvolumes of a dilute aqueous solution of water soluble substances comprising at least partially filling a discrete strand of hollow fiber with said solution, the walls of said fiber containing pores sized to pass water therethrough while preventing passage of said biological molecules, establishing fluid communication between the interior of said strand and a reservoir containing said solution of water soluble substances, allowing additional amounts of solution to be drawn into the fiber as water passes through said wall thereby developing a zone of concentrated solution within said fiber, and recovering the concentrated solution from said zone.

The method as previously described wherein the fiber containing the zone of concentrated solution is in fluid communication with an electrophoresis zone so that on-line transfer of the concentrated solution to the electrophoresis zone occurs and separation of the concentrated solution is carried out in said electrophoresis zone.

DESCRIPTION OF THE DRAWINGS

FIG. 1 shows schematically the different approaches to concentrate a solute by means of a hollow fibre according to this invention. The symbol definitions are as follows: H, hollow fiber; V. vessel, for instance an Eppendorf tube, covered by Parafilm.

A) Concentration of low-molecular-weight compounds or macromolecules by evaporation. With both ends of the fiber open the sample will become contracted in the middle of the fiber.

B) Concentration of low-molecular-weight compounds or macromolecules by evaporation. With one end of the fiber closed the sample will be concentrated at that end.

C) Concentration of macromolecules by the Donnan effect. One end of the fiber closed.

D) Concentration of low-molecular weight compounds by evaporation. One end of the fiber closed. This method also permits enrichment of larger molecules by using fibers of larger porosity, but not so large that the polymer (dextran) molecules can penetrate the wall of the hollow fiber.

FIG. 2 shows the analysis by Hewlett Packard Capillary Electrophoresis (HPCE) of proteins concentrated by Embodiment A (FIG. 1A). Sample: $\beta$-lactoglobulin A and B dissolved in 0.01 M Tris-HCl, pH 8.5 each protein at a concentration of 15 g/ml. Fiber (F1) dimensions: 0.2 mm I.D.×200 mm. Duration of concentration: 20 min. The length of the concentrated protein zone was 6 mm. Desalting: 10 min. The fiber was cut close to one edge of the concentrated sample. A 6-cm buffer segment containing the 6 mm wide concentrated protein zone was then squeezed out onto a sheet of Parafilm and diluted 1: 4 with water (since the sample volumes in HPCE cannot be too small the length of the zone squeezed out was as long as 6 cm). Following this 50-fold dilution of the sample, which had a final volume of about 10 $\mu$l, it was transferred to a vial and analyzed by HPCE (electropherogram a). A blank experiment with non-concentrated sample is presented in b).

FIG. 3 shows the analysis by HPCE of proteins concentrated by Embodiment B (FIG. 1B). Sample: R-Phycoerythrin (8.5 $\mu$g/ml). Fiber (F1) dimensions: 0.7 mm. I.D.×200 mm. Duration of concentration: 20 min under non-active evaporation by means of a fan (b). Length of the concentrated protein zone: 6 mm. The sample in the vial was then exchanged for 0.01 M Tris-HCl, pH 8.5 for a 10 min enrichment of the non-concentrated sample in the fiber. The concentrated 6 mm wide sample zone (0.21 $\mu$l) was desalted for 10 min by immersing the fiber into water, squeezed out of the fiber in a 6 sm long segment, and then diluted with water for analysis by HPCE (a,b). The concentrate protein zone was thus diluted totally 10×2=20 times prior to this analysis. Obviously, the active evaporation gave a much larger enrichment in spite of the shorter concentration time (observe that the scales on the y-axis are different in a) and b)).

Sample: the same as in FIG. 3, although the protein concentration was 15 $\mu$g/ml. Fiber (MC 55) dimensions: see the legend to FIG. 2. Polymer concentration: 15% dextran (mol. wt. 2,000,000) dissolved in 2.5 mM Tris-HCl, pH 8.5. Following concentration for 10 min the sample in the vial was replaced by 0.01 M Tris-HCl butter, pH 8.5. After concentration also of the sample in the fiber (10 min.), dextran adhered to the outside of the fiber was removed by washing with water for 5 sec. The concentrated sample was diluted with 0.01 M Tris-HCl, pH 8.5 totally 10×2=20-fold in a manner similar to that described in the legends to FIGS. 2 and 3. An HPCE analysis gave the electropherogram in a). The analysis was then repeated with the original non-concentrated sample (b).

FIG. 5 shows the analysis by HPCE of low-molecular-weight compounds concentrated by Embodiment D (FIG. 1D). Sample: 200 $\mu$g/ml of $k_2CrO_4$ dissolved in water. Fiber (MC 55) dimensions: 0.2 mm I.D.×270 mm. Duration of the concentration: 20 and 10 min with the fiber surrounded by sample solution and air, respectively. The concentrated sample was diluted 10×2=20 times with 0.01 M Tris-HCl, pH 8.5 as described in the legends to FIGS. 2 and 3, and subjected to an HPCE analysis (a). The experiment was repeated with vitamin $B_{12}$ as sample (100 $\mu$g/ml dissolved in water). Since $B_{12}$ is virtually noncharged it was transported past the detector by the electroendosmotic flow in an uncoated fused silica tubing (c). Blank experiments (without concentration of the sample) are presented in b) and d), respectively.

FIG. 7 shows the analysis by HPCE of proteins concentrated by a combination of Embodiment B and displacement electrophoresis along with a counter flow.
Sample: β-lactoglobulin A (A). β-Lactoglobulin B (B), L-lactalbumin (L) and hemoglobin $A_o$(Hb). For details, see text. The sample was first concentrated using a hollow fiber, diluted 10×5 =50 times and then concentrated by displacement electrophoresis in the capillary mode and finally analyzed by carrier free HPCE (a). By a 50-fold dilution of the sample following the first concentration step the risk was minimized that the concentration limits for the solubility of the proteins were exceeded in the second concentration step. A blank experiment (without concentration of the sample) is presented in b). Observe that the scales on the y-axis are different in a) and b).

FIG. 8 is a schematic drawing showing the concentration method of this invention on-line with the subsequent separation by electrophoresis. The on-line procedure is characterized by:

I. The concentration step

The right end of the capillary is closed. No voltage is applied. During this step the sample will become concentrated at the closed end and at the same time equilibrated with diluted buffer. The other concentration method discussed herein can also be used, but must be followed by equilibration against the diluted buffer.

II. The electrophoresis step

The right end of the capillary is open. Voltage is applied. The concentrated zone at A will migrate into the capillary during zone sharpening and will then be separated into bands by normal electrophoresis means.

DESCRIPTION OF PREFERRED EMBODIMENTS

The water transport through the pores in the fiber wall can be achieved by passive or active evaporation or by the Donnan effect accomplished by immersing the fiber filled with sample into a polymer solution. The method has the advantage to permit concentration of all substances independently of their molecular weight. Proteins, for instance, were enriched 3000-fold in one step. By using an array of fibers and collecting all of the concentrated zones for a second concentration the degree of concentration can theoretically become $3000^2=9\times10^6$-fold, provided that the limit of solubility is not exceeded. The speed of enrichment of proteins was 14-fold per minute for a fiber with the inner diameter 0.2 mm, the length 280 mm and the wall thickness 0.01 mm. The speed can be increased considerably by blowing air over the fiber, for instance, by means of a fan. Simultaneously with the concentration, some purification of the sample can often be achieved by using a fiber with an appropriate molecular-weight cut-off value.

The hollow fibers used in this invention preferably have an inside diameter of about 0.02 mm to about 0.8 mm, more preferably from about 0.1 mm to about 0.8 mm, and typically about 0.2 mm. The wall thickness preferably is about 0.01 mm to about 0.08 mm, and typically, about 0.02 mm. Therefore, water can rapidly pass through the pores of the wall from the inside to the outside of the fiber, for instance, by evaporation or the Donnan effect which operates when the fiber is surrounded by a polymer solution. This removal of water is equivalent to an enrichment of the sample in the hollow fiber. In preferred embodiments of the invention, the pore sizes are adapted to also pass biological molecules having a molecular weight up to about 10,000 daltons, and even more preferably up to about 500,000 daltons. However, at least one end of the hollow fiber must be open during the course of the concentration to accomplish a hydrodynamic flow in the fiber. This flow has two effects: to avoid drying of the fiber and the sample solution and to permit a volume of the sample larger than the inside volume of the fiber to be concentrated by immersing the open end(s) in a vial containing the sample (for details see Embodiment A below).

It should be noted that both high- and low-molecular-weight substances can be concentrated by means of this technique. The invention is particularly applicable to biological molecules such as proteins. For desalting or equilibration of the sample the fiber, filled with the sample, is immersed in an appropriate solution.

Figure 1A:
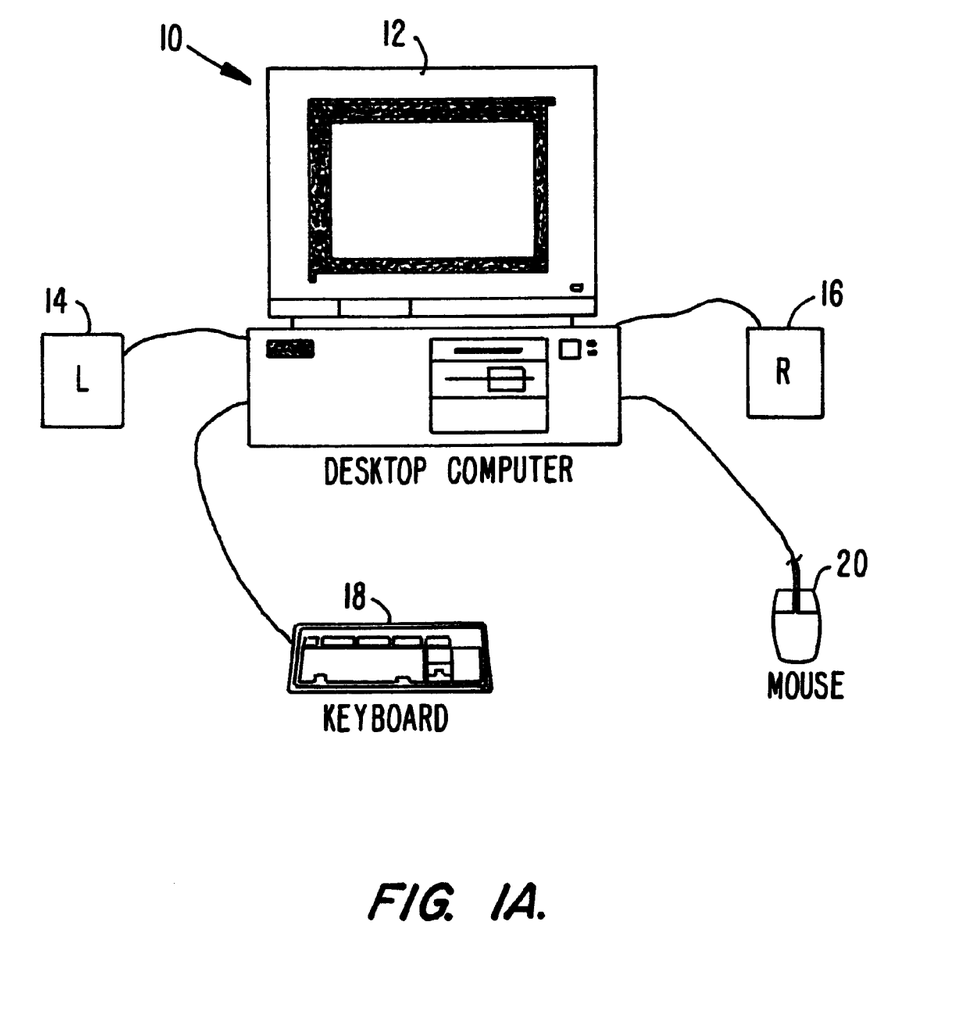

Embodiment A (FIG. 1A). The entire hollow fiber H is filled with the sample. Both ends of the fiber are open and dipped into vials V containing the sample. Evaporation of water through the pores in the fiber wall gives rise not only to an enrichment of the sample but also to a hydrodynamic flow from the vials toward the center of the fibre, where the sample thus will become concentrated. If the sample vials are then exchanged for vials containing buffer or water even the almost non-concentrated sample in the rest of the hollow fiber will be displaced toward the middle section of the fiber and at the same time become concentrated.

Only the fiber is filled with sample (and the sample vials V are omitted) when the volume of the sample is limited or only a lower degree of enrichment is desired.

By blowing air over the fiber, for instance, by means of a fan or reducing the air pressure on its outside, the speed of evaporation of water increases and the time required for the concentration diminishes.

Figure 1B:
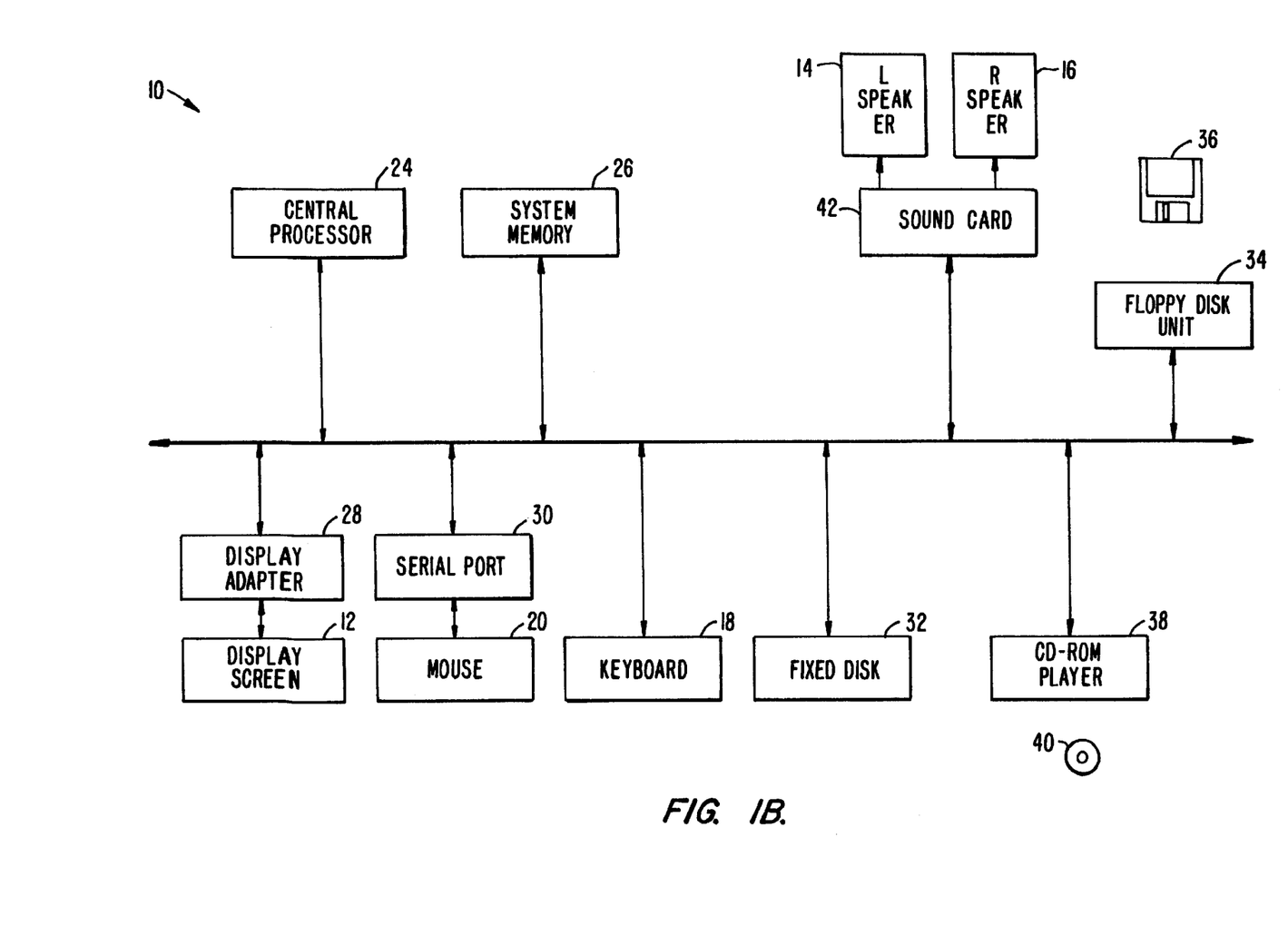

Embodiment B (FIG. 1B). The procedure is the same as in Embodiment A with the difference that one end of the hollow fiber is closed, for instance, by means of a knot, or by inserting the fiber into an Eppendorf tube and locking down the lid. The hydrodynamic flow and thereby the concentration, is directed toward the closed end.

Embodiment C (FIG. 1C). The method resembles that in Embodiment B with the difference that the Donnan effect instead of evaporation is utilized for the removal of water. To accomplish this the fiber is immersed into a solution of a polymer.

Embodiment D (FIG. 1D). This method can be used when the sample consists of solutes small enough to penetrate the walls of the fiber. Part of the fiber, entirely filled with the sample and closed at one end, is immersed in the sample solution. The open end is dipped into a vessel containing water, buffer or sample. Enrichment of the sample takes place by evaporation of water from the right section of the fiber. A lower degree of concentration is obtained if the fiber is filled with sample and is not surrounded by the sample solution. As alternatives to this approach to concentrate substances of low-molecular weight one can, with advantage, employ Embodiments A and B.

Embodiment E: Combination of one of the Embodiments A–D with on-line concentration by displacement electrophoresis and a hydrodynamic counter flow. Following concentration by one of the above four methods the fiber is immersed into the leading solution of a buffer system designed for on-tube concentration by displacement electrophoresis. After this dialysis, which takes 5–10 minutes, the sample is sucked into a coated fused silica tubing for further concentration by displacement electrophoresis, which is automatically transformed into an analysis by free zone electrophoresis. The details of this on-tube concentration method are described in Hjerten, S.; Liea, J. L.; Zhang, R. J. Chromatogr. A 1994, 676, 409 and Liao, J. L.; Zhang, R; Hjerten, S. J. Chromatogr. A 1994, 676 421.

In the following Examples, standard proteins (B-lactoglobulin A and B, α-lactalbumin and hemoglobin $A_o$) were from Bio-Rad Laboratories (Hercules, Calif., USA). R-phycoerythrin, a red acidic protein, was extracted from the red alga Ceramium rubrum and purified as described in Tisellus, A.; Hjertén, S.; Levin Ö. Arch Bioechem. Biophys. 1956, 65, 132. Vitamin $B_{12}$ was bought from Sigma (St. Louis, Mo., USA) and potassium chromate from E. Merck (Darmstadt, Germany). Hollow cellulosic fibers, Cuprophan® F1 5.5 and Hemophan® MC 55 (200 $\mu$m ID, 8 and 21 m wall thickness in the dry and water-wet state, respectively, molecular weight cut-off: 10,000), were a generous gift from AKZO (Obernburg, Germany). Fused-silica tubing (100 $\mu$m ID×35 cm) from Polymicro Technologies (Phoenix, Ariz. USA) were coated with polyacrylamide in order to eliminate electroendosmosis and adsorption of proteins onto the wall of the capillary, Hjerten, S. J. Chromatogr. 1985, 347, 191. The HPCE instruments, BioFocus 3000 and HP$^{3D}$ Capillary Electrophoresis System, were from Bio-Rad Laboratories (Hercules, Calif., USA) and Hewlett Packard (Waldbronn, Germany), respectively. The free zone electrophoresis experiments were performed in 0.1 M Tris-HCl (pH 8.5) at 25° C. and 10 kV. The standard proteins were dissolved in 0.01 M Tris-HCl (pH 8.5) and phycoerythrin was dialyzed against this buffer. The sample was injected hydrodynamically at 50 mbar for 10 sec.

EXAMPLE I

Concentration by Embodiment A (FIG. 1A)

Figure 2A:
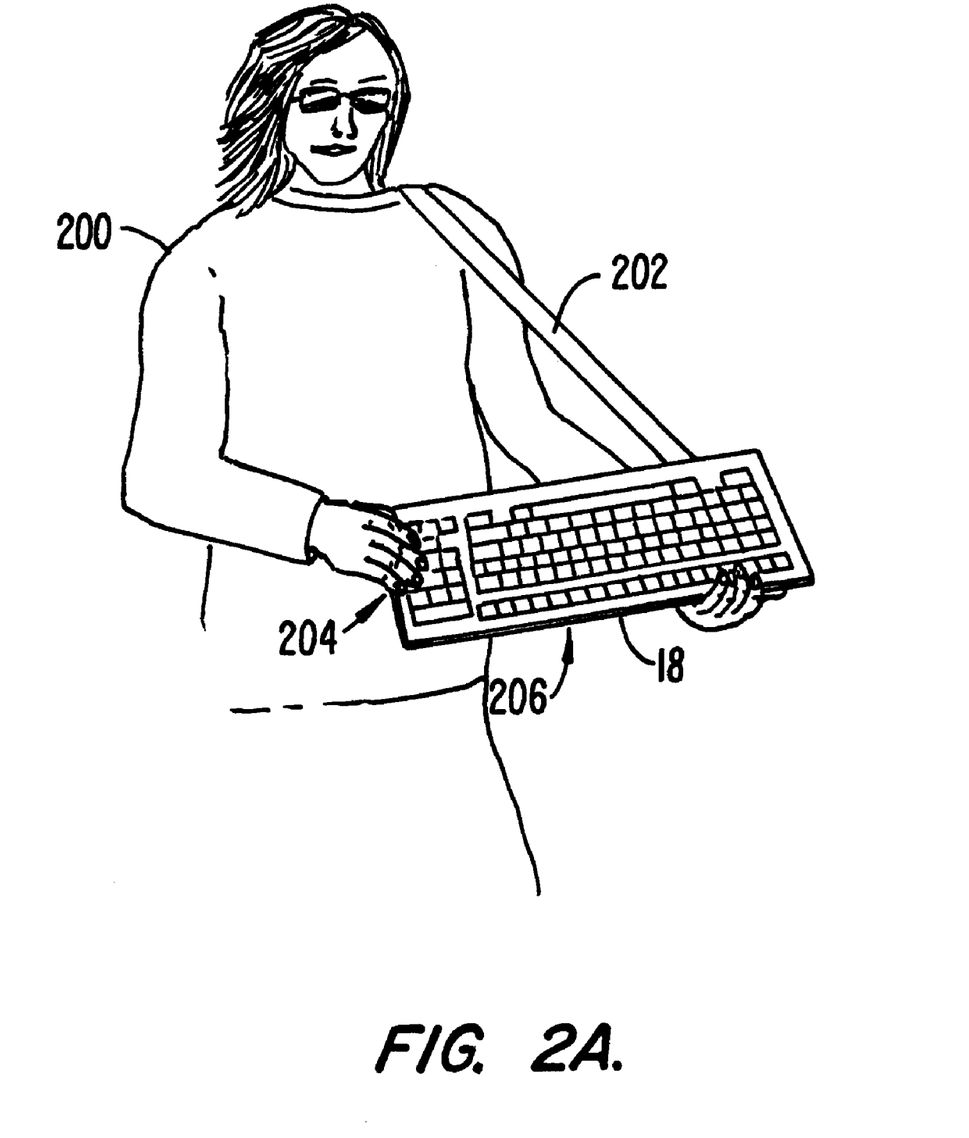
Figure 2B:
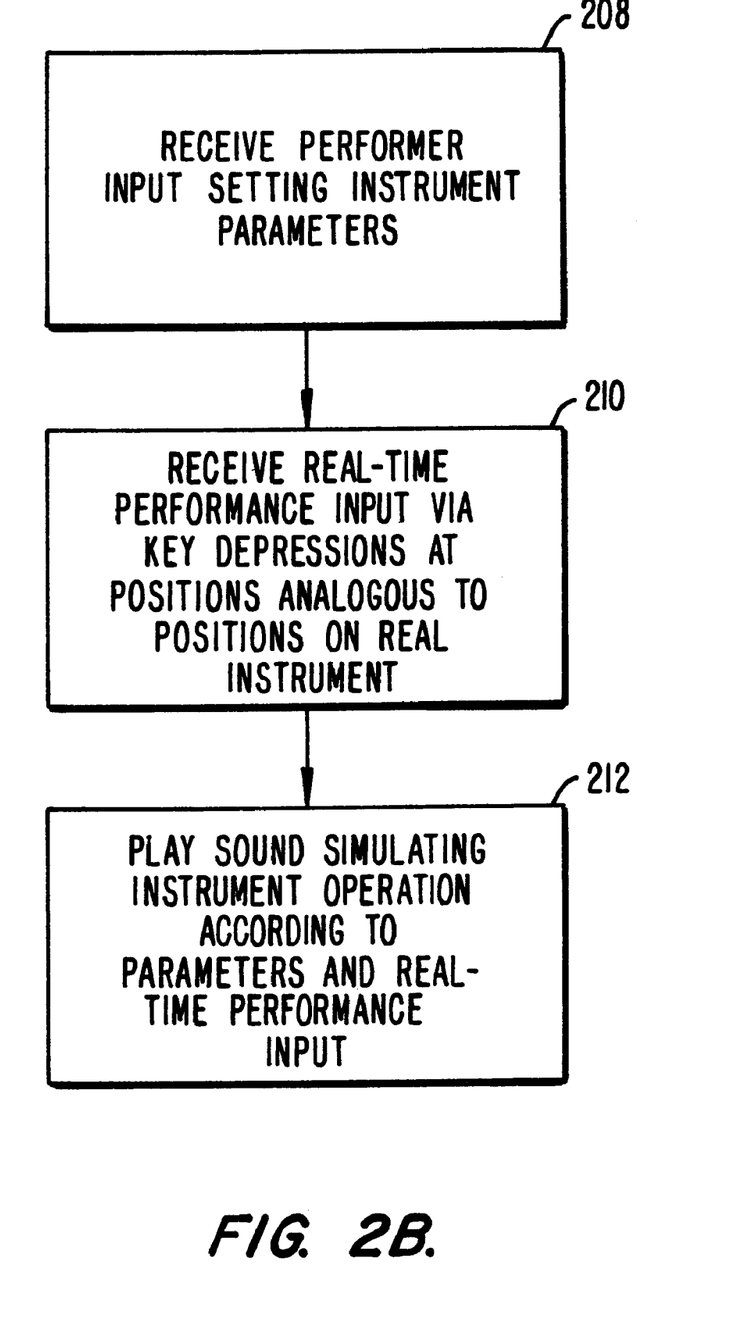

The length of the hollow fiber (F1) was 20 cm. The sample in both vials consisted of β-lactoglobulin A (15 $\mu$g/ml) and β-lactoglobulin B (15 $\mu$g/ml). Following enrichment by passive evaporation for 20 min. as outlined above under "Embodiment A", the sample solution in the vials was exchanged for the 0.01M Tris buffer (see Materials and apparatus) to permit the sample in the fiber to be concentrated for 5 min in the middle of the fiber. The concentrated protein zone was about 6 mm long, as estimated visually from the red color of $B_{12}$ which was added to the sample. Prior to analysis by capillary electrophoresis a few drops of water were placed on the section of the fiber that contained this zone (the fiber rested on a piece of Parafilm). Following this desalting for 10 min the fiber was cut by a pair of scissors at one edge of the protein zone, which, along with a 24 mm wide buffer zone, was then squeezed out onto a piece of Parafilm and diluted 1:4 with water. The 6 mm wide concentrated protein zone was thus diluted 10×5=50=fold. This protein solution and the original, non-concentrated sample were analyzed by high-performance capillary electrophoresis (HPCE). A comparison of the electropherograms in FIGS. 2a and 2b shows the efficiency of the concentration technique. The reason why we collected a 6-cm long zone (approximately 2 $\mu$l) and not only the 6 mm wide concentrated protein zone was that the HP$^{3D}$ Capillary Electrophoresis System requires a sample volume of at least 4 $\mu$l.

EXAMPLE II

Concentration by Embodiment B (FIG. 1B)

Figure 3A:
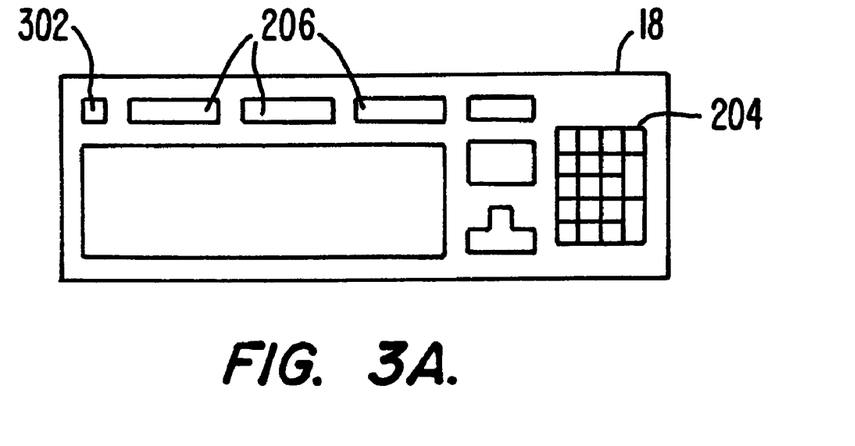
Figure 3B:
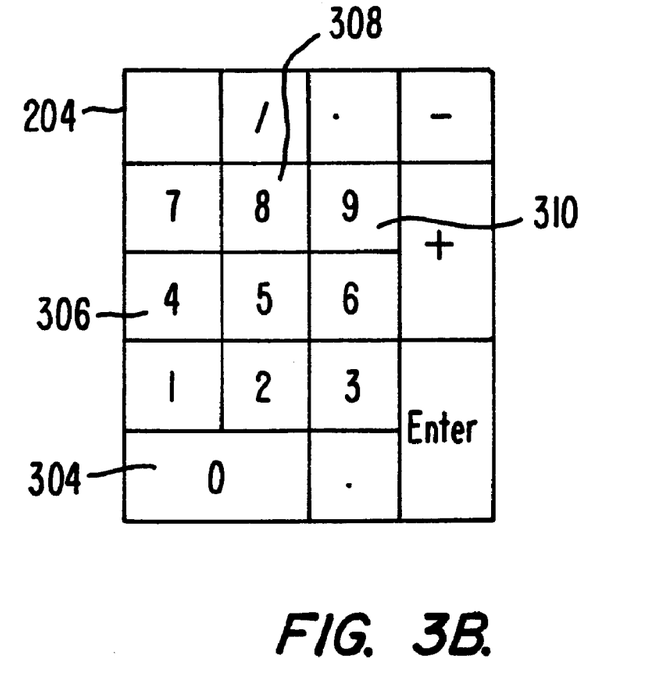

The experimental conditions were similar to those described in the previous section except that the sample consisted of R-phycoerythrin at a concentration of 8.5 $\mu$g/ml and that the evaporation (and thereby the concentration) was speeded up by blowing air for 4 min over the fiber by means of a fan. The electropherogram is presented in FIG. 3b. The protein is heterogeneous, Tisellus, A.; Hjertén, S.; Levin, Ö. Arch. Biochem. Biophys. 1956, 65, 132 and gives a broad protein zone. A similar experiment with non-active evaporation for 20 min gave a 6-fold lower enrichment (FIG. 3a), although the duration of the concentration step was 5-fold longer. The speed of the concentration was thus 6×20/4=30 times higher.

EXAMPLE III

Concentration by Embodiment C (FIG. 1C)

Figure 4:
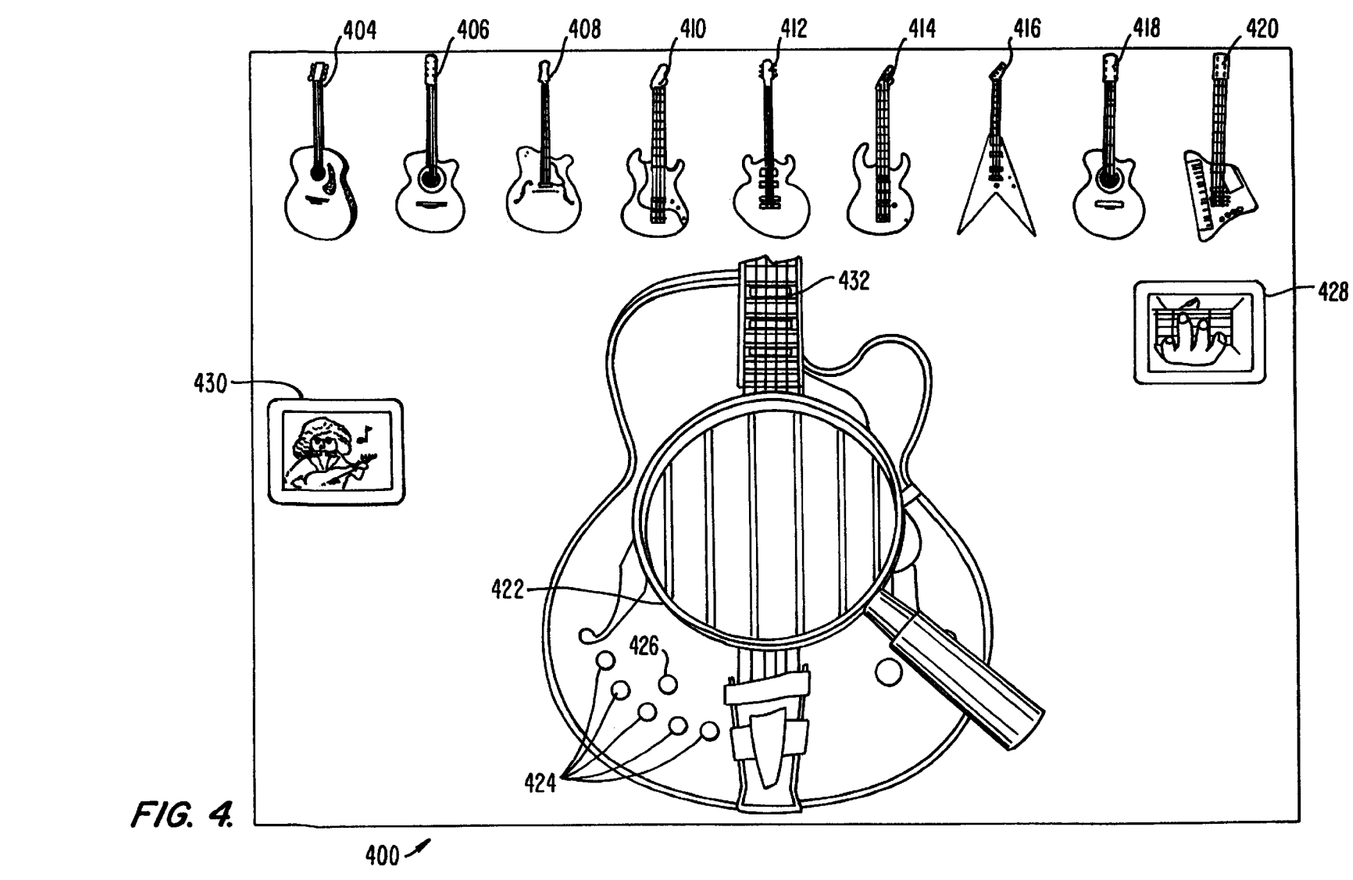
FIG. 4 shows the analysis by HPCE of proteins concentrated and desalted in one step by Embodiment C (FIG. 1C).

R-phycoerythrin (8.5 $\mu$g/ml) was used as model substance. About ¾ of the fiber (MC 55) was surrounded by a 15% solution of dextran (mol. wt. 2,000,000) in 2.5 mM Tris-HCl, pH 8.5, for 10 min (see FIG. 1C). The sample solution in the vial was then replaced by 0.01 M Tris-HCl, pH 8.5 and the concentration was continued for an additional 10 min. The fiber was washed with water for 5 sec to remove dextran on the outside of the fiber. A capillary electrophoretic analysis of the concentrated sample following a 10 ×2=20-fold dilution, as described in section "Concentration by Embodiment A" (FIG. 1A) is shown in FIG. 4a. The method does not require any special step for desalting, since low-molecular weight compounds pass through the fiber wall during the concentration. FIG. 4b shows an electropherogram corresponding to a blank experiment with a non-concentrated sample.

EXAMPLE IV

Concentration by Embodiment D (FIG. 1D)

Figure 5:
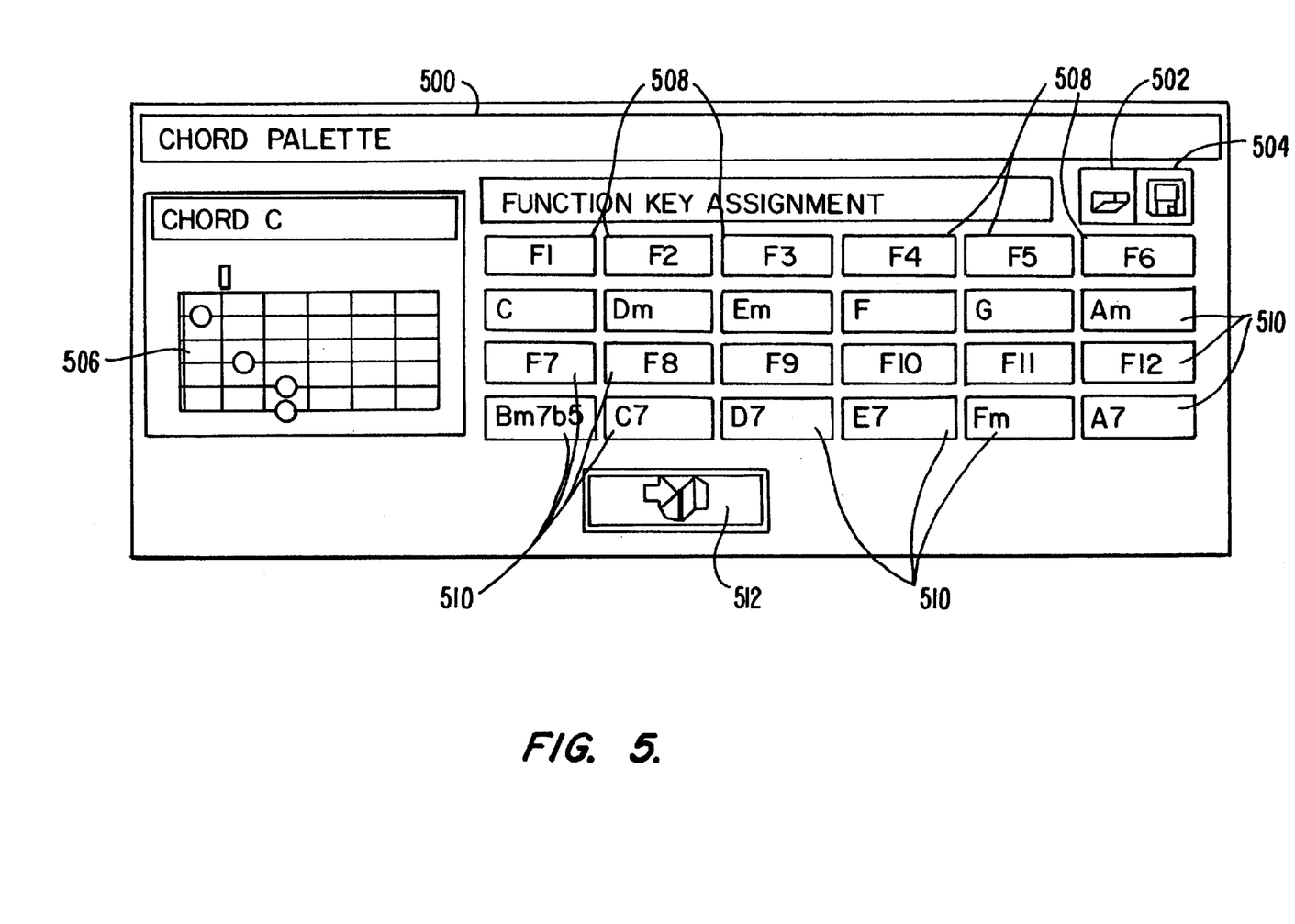

The sample $K_2CrO_4$, was dissolved in water. The concentration was 200 ug $K_2CrO_4$/ml. About one third of the fiber, filled with sample, was immersed into the sample solution for a 20-min concentration and then lifted out of the solution for concentration also of the sample in this third of the fiber, which required 10 min. The enrichment was accomplished by passive evaporation. The 6 mm wide concentrated $K_2CrO_4$-zone was diluted 20-fold with the buffer and studied by capillary electrophoresis in a coated, electroendosmosis-free fused silica tubing (FIG. 5a). A control experiment (without concentration) is shown in FIG. 5b.

Vitamin $B_{12}$ (100 µg/ml) was concentrated in the same way. It is non-charged and consequently does not move in an electric field. Therefore, it was analyzed in a non-coated fused silica tubing by electroendosmatic migration past the detector (FIGS. 5c and d).

EXAMPLE V

Concentration by Embodiment E

The sample consisted of Bio-Rad standard proteins β-lactoglobulin A, β-lactoglobulin B, α-lactalbumin and hemoglobin $A_o$) diluted in 0.015 M HCI-Tris, pH 8.5 to a concentration of 15 µg/ml of each protein (the Buffer concentration refers to that of Tris).

The fiber tubing MC 55 (length: 25 cm) was filled with the sample solution which was concentrated by blowing air over the fiber for 20 min (see Embodiment B). The fiber with the concentrated 6 mm wide protein zone, the volume of which was about 0.2 µl, was immersed in the above buffer for equilibration since this buffer was the leading solution in the subsequent enrichment by displacement electrophoresis. For this step the equilibrated protein zone was diluted totally 10×5=50-fold with the buffer (the procedure was the same as that set forth in the descriptions of FIGS. 2 and 3) and sucked into the coated capillary (100 µm I.D. ×250 mm). The on-line enrichment was performed as described in Hjerten, S.; Liao, J. L.; Zhang, R. J. Chromatogr. A 1994, 676, 409 and Liao, J. L.; Zhang, R.; Hjertén, S. J. Chromatogr. A 1994, 676, 421. The anolyte and catholyte consisted of 0.015 M HCI-Tris, pH 8.5 (700 µl) and 0.01 M glycine-NaOH, pH 8.5 (100 µl), respectively. The buffer concentrations refer to the concentrations of chloride and glycine. The difference between the buffer levels was 20 mm. The enrichment took place at 3000 V for 15 min.

Figure 7:
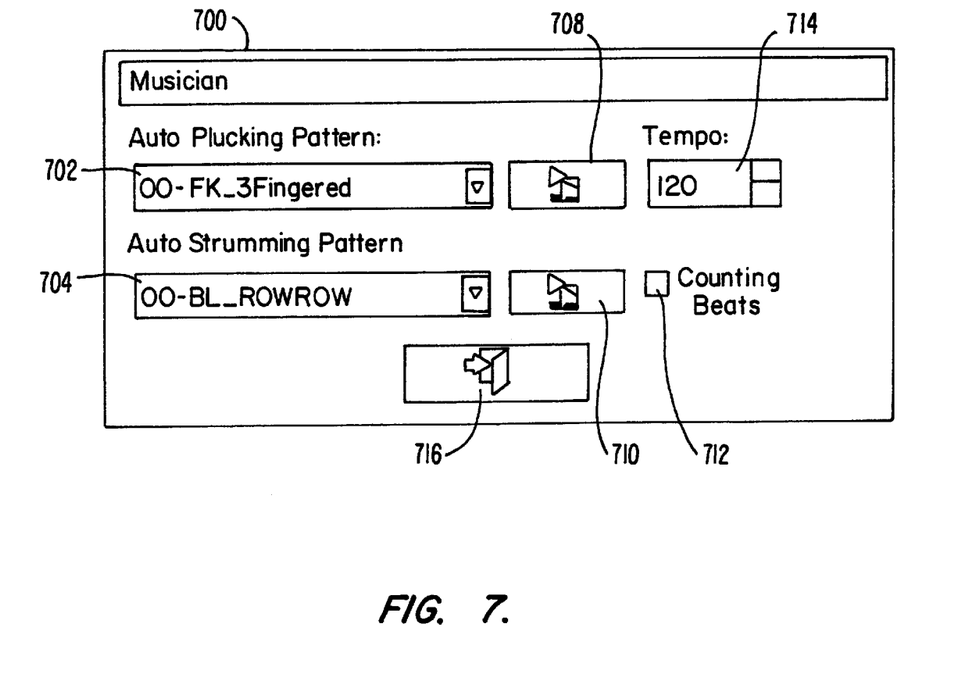

For transformation of this displacement electrophoresis step to an analytical free zone electrophoresis the glycine buffer was replaced by the HCI-Tris buffer. With no difference in the buffer levels, reversal of the polarity and detection at 220 mm the analysis took place at 8000 V for 15 min (FIG. 7).

For these runs, the Bio-Rad HPCE apparatus was used because the Hewlett-Packard instrument does not permit a difference in buffer levels.

EXAMPLE VI

The degree and speed of concentration.

Figure 6:
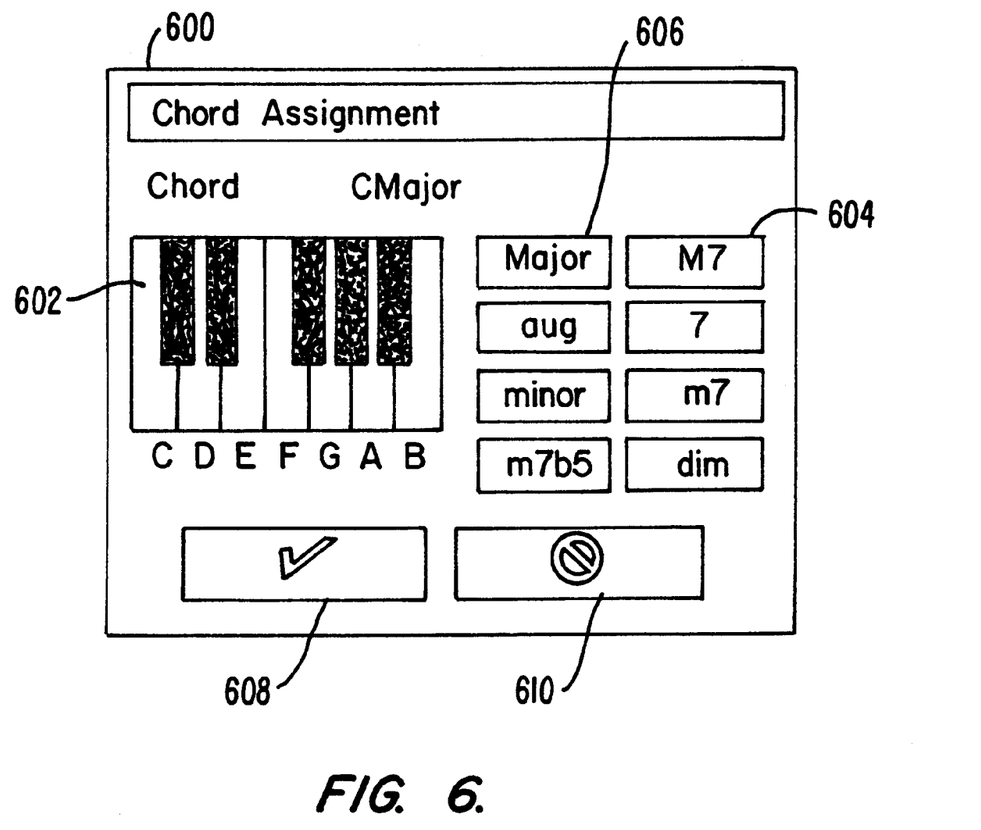
FIG. 6 shows the time required to concentrate a certain sample volume by non-active evaporation according to Embodiment B (FIG. 1B). Sample: 0.85 $\mu$g/ml R-phycoerythrin. Fiber (MC 55) dimensions: 0.2 mm. I.D.× 280 mm. Active evaporation gives a 30-fold more rapid concentration.

The sample, which had a volume of 800 µl, consisted of a colored protein, phycoerythrin. Its concentration was too low to allow visual detection (0.85 µg/ml). For the enrichment we chose Embodiment B. The length of the fiber (MC 55) was 28 cm, which corresponds to a volume of 9 µl (I.D.=0.2 mm). The vial with the sample was weighed every hour to get an estimation of the volume sucked in. This volume is $m_o/d - m_n/d$, where $m_o$ and $m_n$ are the mass of the sample in the vial at the start and after n hours, respectively, and d is the density of the sample solution, which is assumed to be close to 1 µg/µl throughout the concentration procedure. The sample volume sucked in and concentrated at the end of the fiber ($V_n$) can be approximated as $$V_n = m_o - m_n - Vf_f - V_c$$

where $Vf_f$ and $V_c$ are the volumes of the fiber and the concentrated sample zone, respectively. FIG. 6 shows a plot of $V_n$ (eqn. (1)) against time.

EXAMPLE VII

Test for adsorption of proteins onto the fiber wall.

The sample consisted of a 400-µl solution of the red protein R-phycoerythrin. Its absorbance at 500 nm was determined spectrophotometrically in a 1-cm cuvette to be 0.419. It was then concentrated to about 10 µl by Embodiment B and diluted to 400 µl. The absorption was 0.407. The loss of protein that occurred during the concentration procedure was, accordingly, 3%, which might be within the limits of error for absorbance measurements of this kind. For comparison, it should be mentioned that a 10% dilution of the original sample gave the absorption 0.374. Theoretically it should have been 0.419/1.10=0.381, i.e., the measured value was 0.007/0.381–100=2% too low. Although the uncertainty in all these measured values of absorption is obvious, one can conclude that the recovery of protein following concentration in a hollow fibre is high, i.e., the adsorption onto the fiber wall is low.

RESULTS AND DISCUSSION

A comparison between the concentration Embodiments A–D (FIG. 1). The conventional way to desalt a sample or exchange buffers by gel filtration is not applicable to the small sample volumes (<1 l) obtained following concentration by the methods described herein. However, these procedures can easily be executed by immersing the fiber with the concentrated sample zone into water or a dilute buffer. Approach C, utilizing the Donnan effect, has the advantage that this step can be omitted, since removal of low-molecular-weight compounds (dialysis) takes place at the same time as concentration.

All embodiments described work well for the concentration of both low-molecular and macromolecular analytes, except Embodiment D, which is designed only for low-molecular weight compounds.

FIG. 7 shows a combination of the concentration technique described herein and that based on displacement electrophoresis. Other combinations are possible, including solid-phase micro extraction, which is appropriate as the final step for mass spectrometry of proteins, Liao, J. L.; Zeng, C. M.; Hjertén, S.; Pawliszyn, J. J. Microcolumn Separations 1995 8(1),1.

Embodiment A requires the addition of a colored compound, for instance vitamin $B_{12}$, for exact localization of the concentrated zone of a non-colored macromolecule. In the other approaches the sample is enriched at the closed end of the fiber.

Although all of the embodiments A–D (except C) can be used for the concentration of low-molecular-weight-compounds, D is particularly appropriate when the sample also contains macromolecules, for instance proteins, and only the low-molecular weight compounds are to be concentrated. However, when the protein concentration is as high as in serum (about 7%) the Donnan effect gives rise to such a strong flow of water from the inside of the fiber toward its outside that the fiber becomes flat, which virtually stops the enrichment. This problem is overcome if the solution in the fiber contains a polymer. Embodiment D permits selective concentration of solutes with regard to their size, since hollow fibers with different molecular mass cut-off values are commercially available.

The electropherograms in FIGS. 2a and 3a correspond to passive evaporation and that in 3b to active evaporation (by means of a fan), whereas those in FIGS. 2b and 4b were obtained without concentration (blank runs). A comparison of these electropherograms indicates the importance of active evaporation to reduce strongly the duration of the concentration step (about 30-fold).

The degree of concentration. FIG. 6 shows a plot of $V_n$, the volume sucked in and concentrated at the closed end of the fiber (eqn (1)) against time. From the observed length of the colored concentrated sample zone, 6 mm, corresponding to a volume of 0.2 ul, the degree of concentration by passive evaporation after 4 hours can be estimated at 670/0.2=3350-fold, or 3350/(4–60)=14-fold per minute (since samples with a volume as small as 0.2 ul are difficult to handle they were always diluted to about 4 ul (i.e. 20-fold) prior to analysis by capillary electrophoresis). In some cases a 30-fold faster concentration can be achieved by active evaporation (see FIG. 6).

If an array of hollow fibers is used and all of the concentrated zones are combined for a second concentration the enrichment will be $n^2$, where n is the degree of concentration in the first step. For m passages it will be $n^m$. For a 1000-fold concentration in the first step the enrichment in the second step will thus become $10^6$-fold and $10^9$-fold in the third step, provided that the limit of solubility is not exceeded, but if so, the enrichment has been driven unfittingly far.

The fibers used show no or insignificant adsorption of proteins, which is a prerequisite for enrichment of very dilute solutions. Due to this low adsorption and the absence of electroendosmosis the fibers should be ideal also as capillaries in HPCE. However, upon electrophoresis runs in fibers covered by carbon tetrachloride to prevent evaporation of water the zones became relatively broad. There are several reasons for this, for instance convection (due to the large inside diameter of the fiber) and variations in the area of the non-circular cross-section of the fiber. Improved results are attainable using more uniform and somewhat more thick-walled (i.e. rigid) fibers with inside diameters around 50 $\mu$m. A practical advantage of such fibers is that the transfer of the concentrated zone to a capillary for an HPCE analysis can be avoided. However, following enrichment, the concentrated zone should be surrounded by dilute buffer or water for some minutes to get a sharp starting zone in the subsequent electrophoresis in the same fiber, Hjertén, S. Electrophoresis 1990, 11, 665. Another advantage is that the fiber probably does not require a coating to suppress adsorption, which seems to be negligible.

Many analytical and micropreparative methods require a preconcentration or/and a desalting of the sample and often the transfer of the sample to an appropriate milieu, for instance a buffer of an appropriate pH. A sample introduced into a hollow fiber can be concentrated efficiently by spontaneous or forced evaporation of water through the pores in the wall of the fiber or, alternatively, by Donnan transport of water by surrounding the fiber with a polymer solution. The transport of water through the wall of the fiber can be achieved also by vacuum, but this approach is more complicated. A 1000-fold enrichment can be achieved easily. The recovery of the sample is close to 100%. Rapid equilibration of the sample with any particular medium can be achieved by immersing the fiber into that medium.

Figure 8:
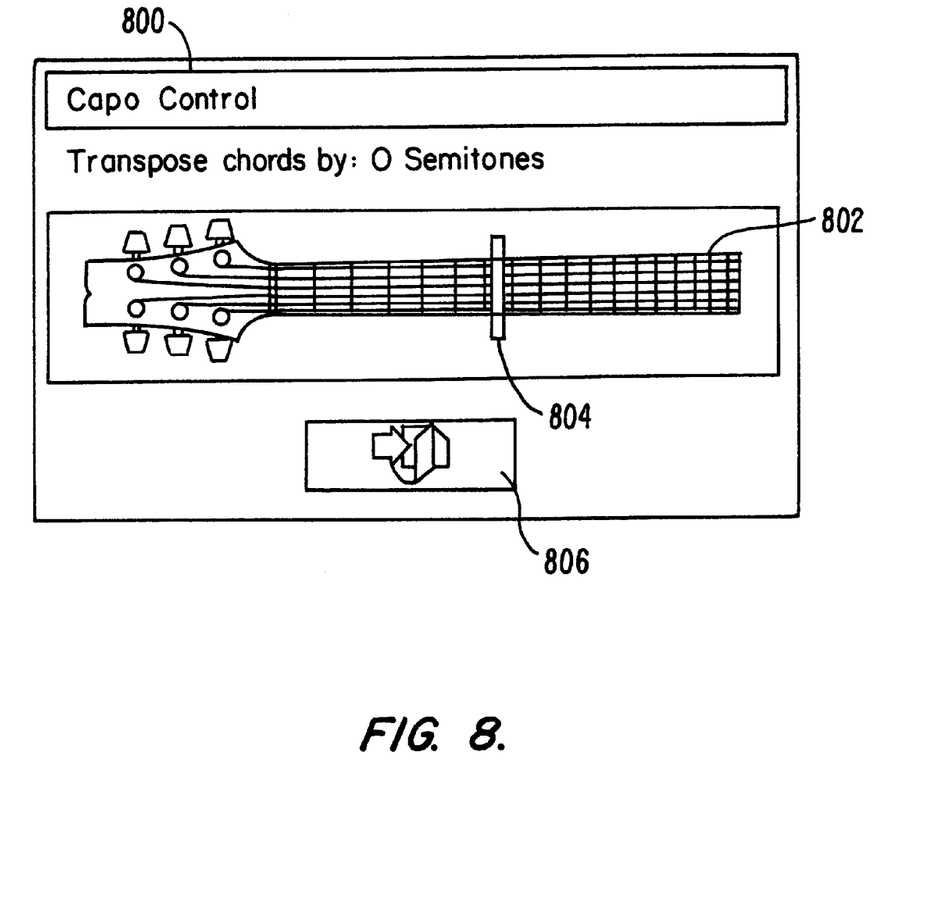

The concentration according to the present invention can be carried in a manner which is on-line with the capillary electrophoresis separation step as shown in FIG. 8. For example, the coated capillary is inserted into the hollow fiber. The hollow fiber should have somewhat thicker walls than those discussed above in order to be more mechanically stable and, therefore, easier to handle. After the coated capillary has been inserted, it is sealed to the hollow fiber with an epoxy glue. Using one of the methods described for concentration and equilibration with the buffer (diluted with water, for instance 1:10) the enriched sample is injected into the capillary, preferably by a pressure difference, one of the standard application techniques in capillary electrophoresis. A sharp starting zone is obtained by the low conductivity of the dilute sample zone.

The invention is defined by the following claims.

I claim:

1. Apparatus for the concentration of microvolumes of a dilute aqueous solution of water soluble substances comprising a discrete strand of hollow fiber adapted to receive an initial amount of said solution, the walls of the fiber containing pores sized to pass water therethrough, and means associated with said strand for replenishing the volume of liquid within the strand by drawing additional quantities of said solution into said fiber solely due to the passage of water through said wall at a rate approximately equal to the rate of water passing through said wall.

2. The apparatus of claim 1 wherein the water soluble substances are biological molecules.

3. The apparatus of claim 1 wherein at least one end of said strand is in fluid communication with a reservoir containing said solution to be concentrated.

4. The apparatus of claim 1 wherein both of the ends of said strand are in fluid communication with reservoirs containing said solution to be concentrated.

5. The apparatus of claim 1 wherein one end of said strand is in fluid communication with a reservoir containing said solution to be concentrated and the other end of the strand is sealed.

6. The apparatus of claim 1 wherein one end of the strand is in fluid communication with a reservoir containing a buffer or sample, the other end of the strand is sealed, and a length of the strand in proximity to the reservoir is immersed in a second reservoir containing said solution to be concentrated.

7. The apparatus of claim 1 wherein the pore sizes are adapted to also pass biological molecules having a molecular weight up to about 10,000 daltons.

8. The apparatus of claim 1 wherein the pore sizes are adapted to also pass biological molecules having a molecular weight up to about 500,000 daltons.

9. The apparatus of claim 1 wherein said hollow fiber has an inside diameter of about 0.02 mm to about 0.8 mm.

10. The apparatus of claim 1 wherein the hollow fiber has a wall thickness of about 0.01 mm to about 0.8 mm.

11. The apparatus of claim 1 wherein the exterior of the strand is exposed to air to permit evaporation of water passing through said wall.

12. The apparatus of claim 1 wherein the exterior of the strand is provided with air circulating means to accelerate the evaporation of water passing through said wall to increase the concentration rate of the solution.

13. The apparatus of claim 1 wherein the exterior of the strand is immersed in a further reservoir adapted to contain a relatively concentrated polymer solution for promoting the passage of water through the walls by the Donnan effect.

14. The apparatus of claim 1 wherein the strand is in fluid communication with an electrophoretic zone for separation of the concentrated solution.

15. The method of concentrating microvolumes of a dilute aqueous solution of water soluble substances comprising at least partially filling a discrete strand of hollow fiber with said solution, the walls of said fiber containing pores sized to pass water therethrough while preventing passage of said biological molecules, establishing fluid communication between the interior of said strand and a reservoir containing said solution of water soluble substances, allowing additional amounts of solution to be drawn into the fiber solely due to the passage of water through said wall at a rate approximately equal to the rate of water passing through said wall, thereby developing a zone of concentrated solution within said fiber, and recovering the concentrated solution from said zone.

16. The method of claim 15 wherein the water soluble substances are biological molecules.

17. The method of claim 15 wherein at least one end of said strand is in fluid communication with a reservoir containing said solution to be concentrated.

18. The method of claim 15 wherein both of the ends of said strand are in fluid communication with reservoirs containing said solution to be concentrated.

19. The method of claim 15 wherein one end of said strand is in fluid communication with a reservoir containing said solution to be concentrated and the other end of the strand is sealed.

20. The method of claim 15 wherein one end of the strand is in fluid communication with a reservoir containing a buffer or sample, the other end of the strand is sealed, and a length of the strand in proximity to the reservoir is immersed in a second reservoir containing said solution to be concentrated.

21. The method of claim 15 wherein the pore sizes are adapted to also pass biological molecules having a molecular weight up to about 10,000 daltons.

22. The method of claim 15 wherein the pore sizes are adapted to also pass biological molecules having a molecular weight up to about 500,000 daltons.

23. The method of claim 15 wherein said hollow fiber has an inside diameter of about 0.02 mm to about 0.8 mm.

24. The method of claim 15 wherein the hollow fiber has a wall thickness of about 0.01 mm to about 0.08 mm.

25. The method of claim 15 wherein the exterior of the strand is exposed to air to permit evaporation of water passing through said wall.

26. The method of claim 15 wherein the exterior of the strand is provided with air circulating means to accelerate the evaporation of water passing through said wall to increase the concentration rate of the solution.

27. The method of claim 15 wherein the exterior of the strand is immersed in a further reservoir adapted to contain a relatively concentrated polymer solution for promoting the passage of water through the wall by the Donnan effect.

28. The method of claim 1 wherein the concentrated solution from said zone passes on-line into an electrophoresis zone wherein the concentrated solution is separated into its component parts.

* * * * *